United States Patent [19]

Ampleman

[11] Patent Number: 5,124,463
[45] Date of Patent: Jun. 23, 1992

[54] SYNTHESIS OF A DIAZIDO TERMINATED ENERGETIC PLASTICIZER

[75] Inventor: Guy Ampleman, St. Augustin de Desmaures, Canada

[73] Assignee: Her Majesty the Queen in right of Canada as represented by the Minister of National Defence, Canada

[21] Appl. No.: 601,316

[22] Filed: Oct. 23, 1990

[30] Foreign Application Priority Data

Jan. 19, 1990 [CA] Canada ................... 2008154

[51] Int. Cl.$^5$ ........................................ C07C 247/04
[52] U.S. Cl. ................................................... 552/11
[58] Field of Search .......................................... 552/11

[56] References Cited

U.S. PATENT DOCUMENTS

| 4,486,351 | 12/1984 | Earl | 552/11 |
| 4,781,861 | 11/1988 | Wilson et al. | 552/11 |
| 4,891,438 | 1/1990 | Ahad | 552/11 |
| 4,937,361 | 6/1990 | Wagner et al. | 552/11 |
| 4,962,213 | 10/1990 | Frankel et al. | 552/11 X |

Primary Examiner—Joseph P. Brust
Attorney, Agent, or Firm—Nixon & Vanderhye

[57] ABSTRACT

Glycidyl azide polymer is a hydroxy-terminated aliphatic polyether containing alkyl azide groups. Such a polymer could be used as a plasticizer in composite explosives, gun and rocket propellants. However, the hydroxyl groups of the polymer react with the isocyanate of the curing agent, thereby eliminating any possible plasticizing effect. This problem is overcome by producing a diazido-terminated glycidyl azide polymer without terminal hydroxyl groups. This useful polymer is produced by reacting polyepichlorohydrin with p-toluenesulfonyl chloride in pyridine, and reacting the resulting tosylated polyepichlorohydrin with sodium azide in dimethylformamide.

8 Claims, No Drawings

SYNTHESIS OF A DIAZIDO TERMINATED ENERGETIC PLASTICIZER

This invention relates to a glycidyl azide polymer without terminal hydroxyl groups a process for preparing such polymer and to the use of such a polymer as a plasticizer in composite explosives, gun and rocket propellants.

In research relating to composite explosives and propellants, the inventor has determined that glycidyl azide polymer with a molecular weight of 500 would be useful as a plasticizer in such compositions. The plasticizer serves to enhance the stability and mechanical properties of the compositions. Unfortunately, the hydroxyl groups of the glycidyl azide polymer react with the isocyanate curing agent normally used in such compositions, whereby any possible plasticizing effect is lost. In order to avoid this problem, it is desirable to provide a plasticizer without hydroxyl groups.

An azide-terminated azide polymer is disclosed by U.S. Pat. No. 4,781,861, which issued to E. R. Wilson et al on Nov. 1, 1988. The patented azide compound is structurally different and is produced by a method different from the polymer disclosed herein.

An object of the present invention is to meet the above defined need by providing a glycidyl azide polymer which is free of hydroxyl groups, and which consequently can be used as a plasticizer in composite explosives, and gun and rocket propellants.

Another object of the invention is to provide a process for producing a glycidyl azide polymer which is free of hydroxyl groups.

According to one aspect, the invention relates to a process for preparing a glycidyl azide polymer free of terminal hydroxyl groups comprising the steps of tosylating polyepichlorohydrin; and reacting the resulting polyepichlorohydrin tosylate with an alkali metal azide.

According to another aspect, the invention relates to a glycidyl azide polymer free of terminal hydroxyl groups, i.e. a diazide terminated glycidyl azide polymer.

In general terms, the process of the present invention proceeds as follows:

STEP 1:

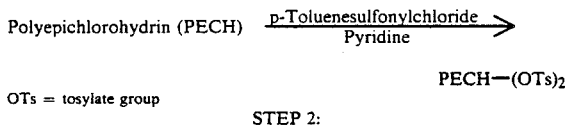

STEP 2:

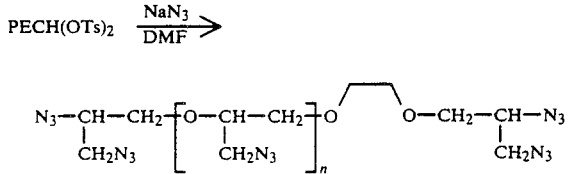

This invention will be described in greater detail with reference to the following specific example of the preparation of the polymer.

EXAMPLE

Step 1

20 g (0.04 mole) of polyepichlorohydrin is added to 200 ml of anhydrous pyridine in a 500 ml three neck flask equipped with a reflux condenser surrounded by an anhydrous calcium chloride tube under an inert atmosphere of argon. 31.748 g (0.1665 mole) of p-toluenesulfonyl chloride is added, and the solution is heated at 60° C. for two hours, followed by agitation at room temperature for twenty-four hours. The mixture thus produced is poured onto 500 g of crushed ice, and acidified with concentrated hydrochloric acid until the pH is acidic. The aqueous solution is extracted with methylene chloride (3×200 ml). The organic combined extracts are washed with water (3×200 ml), dried over anhydrous magnesium sulfate, filtered and evaporated. The 30.13 g (92%) residual oil is used for the second step without further purification.

The infrared and proton nuclear magnetic resonance analysis of the product are as follows:

IR: $\gamma$ max (NaCl) cm$^{-1}$:3080–3020, 2960–2880, 1600, 1495, 1430, 1360, 1190, 970, 820.

'HNMR: $\delta$ (CdCl$_3$) PPM: 7.59 (8H, AB system, $J_{AB}$=8.2 Hz, aromatic protons) 4.70 (2H, p, CHOTS) 3.84–3.56 (m, all other protons), 2.46 (6H, s, CH$_3$ $-\phi$).

In the foregoing, IR=infrared, ' HNMR=proton nuclear magnetic resonance, J=coupling constant, p=pentuplet, m=multiplet massif and s=singulet.

Step 2

30 g (0.038 mole) of polyepichlorohydrin tosylate is dissolved in 550 ml of N,N,-dimethylformamide and the solution is heated to 85° C. in a 2000 ml three neck flask equipped with a thermometer and a reflux condenser. 37.093 g (0.5706 mole) of sodium azide is added to the solution, and the temperature is maintained at 100° C. for forty-eight hours. The mixture is cooled to room temperature and 600 ml of water is added. After a short period of time, 100 ml of methylene chloride is added and separation is effected. The aqueous phase is extracted with methylene chloride (2×150 ml) and the combined organic extracts are washed with water (3×800 ml). The methylene chloride portion is concentrated to 30 ml and again washed with water (3×50 ml). The organic phase is dried over anhydrous magnesium sulfate, filtered and evaporated. 20.45 g of (95% ) polymeric azide is isolated as a yellow oil. The results of analysis of the product are as follows:

IR: $\gamma$ max (NaCl) cm$^{-1}$: 2920, 2880, 2100, 1450, 1290, 1120, 940, 900.

'HNMR: $\delta$ (CdCl$_3$) PPM: 3.75–3.38 (m, all protons).
$^{13}$CNMR: $\delta$ (CdCl$_3$) PPM: 78.79, 78.73 (CHO) 70.85–69.69 (CH$_2$O), 60.69 (CHN$_3$) 53.35–51.50 (CH$_2$N$_3$).

In the above, $^{13}$CNMR=carbon-13 nuclear magnetic resonance.

Elemental analysis of the product yields the results: C (34.8); H(5.0); N(47.2).

Nitrogen analysis of the plasticizer confirms that quantitative azidation of the polyepichlorohydrin tosylate is achieved. The absence of signal for CH$_2$Cl in the $^{13}$CNMR sprectrum equally confirms a complete azidation. The signal for CHN$^3$ in the $^{13}$CNMR sprectrum shows that all tosylate groups are substituted by azide groups. A hydroxyl equivalent weight (Me) of 14077 g/mole is determined by ' HNMR spectroscopy. This value indicates that there is no hydroxyl group in the polymer. The glass transition temperature (Tg) for the polymer is $-73°$ C.

The method described above provides a polymer with no hydroxyl group. Accordingly, the polymer cannot react with the isocyanates used to cure the binder in composite formulations, and the polymer maintains its plasticizer properties.

Thus, there has been described a new product which can be efficiently synthesized at low cost, which is a compatible plasticizer for use in composite explosives, gun and rocket propellants, and which has a low glass transition temperature.

The embodiments of the invention in which an exclusive property or privilege is claimed are defined as follows:

1. A process for preparing a glycidyl azide polymer of the formula:

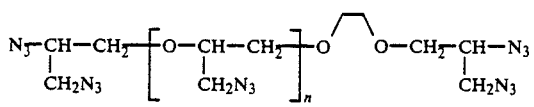

where n is 2 to 28 comprising the steps of
(1) reacting polyepichlorohydrin with p-toluenesulfonyl chloride in the presence of pyridine in an inert atmosphere for a time sufficient to tosylate the polyepichlorohydrin; and thereafter
(2) reacting the tosylate thus produced with an alkali metal azide by heating a mixture of the tosylate and azide until the glycidyl azide polymer is prepared.

2. The process of claim 1, wherein the polyepichlorohydrin is reacted in step (1) initially at 60° C. for two hours followed by agitation at room temperature for 24 hours.

3. The process of claim 1, wherein the inert atmosphere is argon.

4. The process of claim 1, wherein the alkali metal azide is sodium azide.

5. The process of claim 1, wherein the tosylated polyepichlorohydrin is reacted in step (2) with the alkali metal azide at a temperature in the range of 85° to 100° C. in a solvent.

6. The process of claim 5, wherein the solvent is N,N-dimethylformamaide.

7. The process of claim 1, wherein n is 2 to 18.

8. The process of claim 7, wherein n is 2.

* * * * *

UNITED STATES PATENT AND TRADEMARK OFFICE
CERTIFICATE OF CORRECTION

PATENT NO. : 5,124,463
DATED : June 23, 1992
INVENTOR(S) : Guy AMPLEMAN

It is certified that error appears in the above-identified patent and that said Letters Patent is hereby corrected as shown below:

Column 1, line 59, insert the following: --wherein $\underline{n}$ is 2 to 28, preferably 2 to 18, and for the polymer to have a molecular weight of 500 $\underline{n}$ is 2.--.

Column 2, lines 17 and 46, delete $\nu$ (gamma) and insert -- $\nu$ -- (nu).

Signed and Sealed this

Twenty-eighth Day of September, 1993

Attest:

BRUCE LEHMAN

*Attesting Officer*    *Commissioner of Patents and Trademarks*